US007988849B2

(12) United States Patent
Biewer et al.

(10) Patent No.: US 7,988,849 B2
(45) Date of Patent: Aug. 2, 2011

(54) CUSTOMIZABLE PERSONAL DIALYSIS DEVICE HAVING EASE OF USE AND THERAPY ENHANCEMENT FEATURES

(75) Inventors: John A. Biewer, Palm Harbor, FL (US); Andrey Kopychev, Clearwater Beach, FL (US); Merrick F. Kossack, Arlington Heights, IL (US); Philip J. D'Almada Remedios, Palm Harbor, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 471 days.

(21) Appl. No.: 12/132,455

(22) Filed: Jun. 3, 2008

(65) Prior Publication Data
US 2009/0294339 A1 Dec. 3, 2009

(51) Int. Cl.
*B01D 61/31* (2006.01)
*B01D 61/30* (2006.01)

(52) U.S. Cl. ............ 210/94; 210/85; 210/86; 210/87; 210/138; 210/143; 210/258; 210/321.6; 210/646; 604/4.01; 604/29; 604/65; 345/156; 345/173; 353/122

(58) Field of Classification Search .............. 210/85, 210/87, 96.2, 138, 141, 143, 321.6, 646, 210/86, 94, 258; 604/4.01, 5.01, 6.01, 6.09, 604/29, 65; 345/156, 173; 353/122
See application file for complete search history.

(56) References Cited

U.S. PATENT DOCUMENTS

| 4,370,983 A * | 2/1983 | Lichtenstein ............. 600/301 |
| 4,618,343 A | 10/1986 | Polaschegg |
| 5,004,459 A | 4/1991 | Peabody et al. |
| 5,326,476 A * | 7/1994 | Grogan et al. ............ 210/646 |
| 5,412,189 A | 5/1995 | Cragun |
| 5,421,823 A | 6/1995 | Kamen et al. |
| 6,558,343 B1 | 5/2003 | Neftel |
| 7,033,539 B2 | 4/2006 | Krensky et al. |
| 7,410,475 B2 | 8/2008 | Krensky et al. |
| 2003/0218623 A1 * | 11/2003 | Krensky et al. ........... 345/700 |
| 2005/0070778 A1 | 3/2005 | Lackey et al. |
| 2007/0165020 A1 | 7/2007 | Haueter |
| 2008/0094589 A1 * | 4/2008 | Panitz ...................... 353/122 |
| 2008/0097283 A1 | 4/2008 | Plahey |
| 2008/0193919 A1 | 8/2008 | Jung et al. |

FOREIGN PATENT DOCUMENTS

| DE | 33 33 362 | 4/1985 |
| EP | 402 505 | 12/1990 |
| EP | 0 498 382 | 8/1992 |

OTHER PUBLICATIONS

I-Tech Virtual Laser Keyboard. Datasheet [online]. I-Tech [retrieved on Aug. 18, 2008]. Retrieved from the Internet: <URL: www.virtual-laser-keyboard.com.
International Search Report and Written Opinion for International Application No. PCT/US2009/045812 mailed on Dec. 7, 2009.

* cited by examiner

*Primary Examiner* — Joseph W Drodge
(74) *Attorney, Agent, or Firm* — K&L Gates LLP

(57) ABSTRACT

A peritoneal dialysis machine includes an enclosure; dialysate pump located within the enclosure; a graphical user interface connected to the enclosure and configured to display a parameter associated with the dialysate pump; and a projector configured to project the parameter onto a surface external from the enclosure so as to allow a patient to readily view the parameter.

19 Claims, 8 Drawing Sheets

Dwell Distribution #1

| Dwell 1 | 34% |
|---|---|
| Dwell 2 | 33% |
| Dwell 3 | 33% |

Dwell Distribution #2

| Dwell 1 | 40% |
|---|---|
| Dwell 2 | 30% |
| Dwell 3 | 30% |

Dwell Distribution #3

| Dwell 1 | 48% |
|---|---|
| Dwell 2 | 32% |
| Dwell 3 | 20% |

FIG. 8

Timer Function

You have selected the timer function.
Please use keypad to enter:

Timer Start Time: [AM] [PM] ○:○__ __

And

Timer Countdown Time: ○:○__ __

| 1 | 2 | 3 |
|---|---|---|
| 4 | 5 | 6 |
| 7 | 8 | 9 |
| AM | 0 | PM |

Enter

FIG. 9

Calendar Function

You have selected the calendar function. Touch a date to make it enlarge to view or modify. Use keyboard to modify. Touch enlarged date when done to minimize. Days having entries will show entries upon power-up.

◁ | J | F | M | A | MAY | J | J | A | S | O | N | D | ▷

| | Sun | Mon | Tues | Wed | Thurs | Fri | Sat | |
|---|---|---|---|---|---|---|---|---|
| M A Y 2 0 0 7 | | | 1 | 2 | 3 | 4 | 5 | M A Y 2 0 0 7 |
| | 6 | 7 | 8 | 9 Doctor | 10 | 11 | 12 | |
| | 13 | 14 | 15 | 16 | 17 | 18 | 19 Babysit | |
| | 20 | 21 | 22 Birthday | 23 | 24 | 25 | 26 | |
| | 27 | 28 | 29 Vacation | 30 Vacation | 31 Vacation | | | |

CUSTOMIZABLE PERSONAL DIALYSIS DEVICE HAVING EASE OF USE AND THERAPY ENHANCEMENT FEATURES

BACKGROUND

The examples discussed below relate generally to medical fluid delivery. More particularly, the examples disclose systems, methods and apparatuses for dialysis, such as automated peritoneal dialysis ("APD") and hemodialysis ("HD").

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow for the dialysate to dwell within the cavity and for the transfer of waste, toxins and excess water to take place. The source can be multiple sterile dialysate solution bags.

APD machines pump spent dialysate from the peritoneal cavity, through the catheter, to the drain. As with the manual process, several drain, fill and dwell cycles occur during dialysis. A "last fill" occurs at the end of APD, which remains in the peritoneal cavity of the patient until the next treatment.

While APD has obvious lifestyle benefits over CAPD, there is still a need to make dialysis treatments more patient friendly. Also, there are ongoing attempts to bring blood-based dialysis, e.g., HD into the patient's home rather than a center. The embodiments of the present disclosure attempt to address user ergonomics for both types of treatment.

SUMMARY

The embodiments described herein discuss a dialysis machine, such as a peritoneal dialysis machine. The machine includes many features and apparatuses that make the dialysis treatment more palatable and personalized, easier to learn and use, and less prone to error.

In one primary embodiment the peritoneal dialysis machine includes a projector or scanning laser that projects therapy information or other information onto a surface external to the dialysis instrument, such as a ceiling, wall, piece of furniture, etc. The information can be displayed with relatively large text, so that the patient or caregiver can more readily see the information. The information can also be projected onto a surface that allows the patient or caregiver to view the information without having to turn towards the dialysis instrument.

The projected information can include treatment information such as pump fill, dwell and drain information. For example, if the instrument is currently filling the patient, the projector can display onto the remote surface the total fill volume and the amount of the fill that has currently taken place. This can be done quantitatively (via the display of numbers) or pictorially, e.g., via a volume representing total fill, which incrementally changes color indicating current fill level.

Other information can include for example total number of exchanges, current exchange, current time, time remaining for treatment, total ultrafiltration ("UF") to be removed, amount of UF currently removed, ambient temperature, dialysate temperature and other information as desired.

The projector in one embodiment is provided in addition to like information displayed by a display device, which is part of the overall graphical user interface of the dialysis instrument. For example, the display device can display information during therapy, a portion or all of which is projected onto a room wall or other surface. The instrument in one embodiment includes a switch that allows the patient or caregiver to turn the projector on and off. The switch can be located on the machine or be a remote switch (tethered or wireless) that allows the patient to display the information when desired.

In another primary embodiment, the dialysis instrument takes proactive steps to ensure that the patient's prescribed therapy is completed by a time specified by the patient or caregiver. For example, the patient may need to wake-up by 7:00 AM for work. The patient's dialysis therefore needs to be completed by such time and indeed may require additional time for patient disconnection.

In one implementation, the fill time, dwell time, drain time are set, e.g., by a physician. The fill time and drain time can be set directly or by setting fill/drain volume and pump rate. In either case, the total treatment time is set. Here, the dialysis instrument can be configured to alarm or alert when it is time to begin treatment so as to finish on time, e.g., at 7:00 AM. The alert can be an audio, visual, audiovisual alert or tactile (e.g., a vibrating alert on a wearable remote vibrator).

In another implementation, the patient's dwell time is variable. Here, the instrument automatically adjusts the dwell time to attempt to make the treatment end by the prescribed time, e.g., 7:00 AM. The machine can be configured to dwell as long as possible, while completing therapy by the presented time. The machine can be set to have a minimum dwell time such that machine has to dwell for at least the minimum time. Each dwell can be set to be the same duration or to have different durations. For example, the first dwell can be longer than the second dwell, and so on.

In another primary embodiment, the dialysis machine provides additional modes of input for helping the patient control the dialysis therapy including the pumping of dialysate to and from the patient. For example, the machine can include a projector that projects a virtual keyboard display onto a surface, such as a board or book, or machine resting surface, so that the keys are larger than is possible on the dialysis instrument. The patient or caregiver uses the projected keyboard to enter information into the dialysis machine. The patient presses buttons on the virtual keyboard to enter information into the peritoneal dialysis machine, such as therapy information or text that is sent from the dialysis instrument over an internet as electronic mail. The projector in one embodiment is mounted to or rested on the surface onto which the virtual keyboard is displayed. The present system includes a board with a holding apparatus into which the virtual projector is snap-fitted. The board can be tilted for use in the patient's bed or chair without the projector coming free from the board.

In another implementation, the instrument includes a touch screen interface that provides tactile feedback. The tactile feedback is provided for example by molding tactile bumps or information into the tactile overlay itself, into a separate sheet that is applied on top of the touch screen overlay or as epoxy beads that are screen printed onto the touch screen overlay. The touch screen overlay is then attached to the video monitor in the standard manner. The tactile bumps are located at set X-Y areas on the video monitor. However, different information can be displayed at different times on the video monitor for the same touch screen tactile bump.

In a related implementation, the instrument includes a Braille user interface. The Braille user interface can be set at the factory or inserted onto or over a standard user interface. The Braille keys or characters can be provided via the touch screen tactile feedback bumps disclosed herein. The Braille keys or characters can be numbers for entering data or answer words, such as "yes" and "no", which are pressed to answer questions posed by the dialysis instrument, e.g., during therapy setup.

In still another implementation, the instrument includes a telecommunications device for the deaf ("TDD") user interface for deaf or hearing impaired patients. Here, the dialysis instrument incorporates a keyboard (hard or touch screen) and a screen, such as an LED or LCD screen to display typed text electronically. Text is transmitted to the screen live, e.g., via telephone line or cable connected to the dialysis instrument. The patient can respond using the keyboard to enter information, which the TDD converts to audible sounds that are transferred over the phone line. The dialysis instrument can also provide voice guidance information to the user, which a deaf or hearing impared person cannot hear. It is also contemplated to allow voice guidance to be deactivated and for the instructions to be displayed instead on the instrument screen.

In a further primary embodiment, the present disclosure includes a graphical user interface ("GUI") having ease of use, ease of learning, patient preference and patient assist features. For example, the dialysis system can have an alarm clock, which provides a therapy start alert as described above. The clock in one embodiment includes a timer that allows the patient to set a time for a certain procedure such as a mid-day exchange. The user interface in another implementation includes an audio-in connector, so that the patient can use speakers provided in the instrument for external sound-producing devices. Alternatively or additionally, the instrument includes an audio-out connection, which enables the instrument audio to be played on external speakers.

It is also contemplated the instrument with an audio option to play soothing or relaxing music or sounds during therapy.

Still further, the instrument can have patient assist lighting, such as a night light or reading light.

In one embodiment, the GUI includes a calendar that allows patients to insert important therapy information at certain dates, such as doctor visit time and date, effluent sample taking dates, or non-therapy related dates.

It is yet further contemplated to allow the patient to customize the instrument for example by allowing the patient to set a screen-saver, wall paper and/or background for the GUI.

In yet another primary embodiment of the present disclosure, the instrument enclosure or housing is provided with patient assist and customizable features. For example, the enclosure in one implementation has a utensil holder, such as a vase for flowers, which doubles as a pen holder. The enclosure in one embodiment includes a grip-assist device, which aids patients, e.g., elderly patients in removing caps from bottles. Similarly vein, the enclosure includes fingers or other apparatuses to remove pull-caps from containers and/or a device that aids the patient in breaking a tubing frangible. The enclosure can further include a supply drawer and a clamp for temporary disconnection of the patient from the dialysis instrument.

The instrument enclosure of the present disclosure can also be customized for the patient. The bezel around the GUI is interchangeable with a plurality of different bezels so that the patient can choose a desired bezel. It is also contemplated to provide different colored covers so that the patient can choose a desired color, e.g., one that matches a room in which the instrument is likely to be used. Besides color, the decorative bezel/panel can also simulate various material patterns and finishes (e.g., wood, stone, floral pattern, etc.) to match the patient's domestic environment.

It is therefore an advantage of the present disclosure to provide a dialysis instrument that is easier for the patient to learn, use and customize.

It is another advantage of the present disclosure to provide an instrument that assists hearing impaired patients.

It is a further advantage of the present disclosure to provide an instrument that assists patients with visual impairments, hearing impairments and manual dexterity impairments (e.g., in the latter case to provide devices that remove caps and break frangibles)

It is a further advantage of the present disclosure to provide a dialysis instrument that the patient can customize.

Additional features and advantages are described herein, and will be apparent from, the following Detailed Description and the figures.

BRIEF DESCRIPTION OF THE FIGURES

FIG. 8 is an elevation view illustrating a timer function screen for a dialysis system of the present disclosure.

FIG. 9 is an elevation view illustrating a calendar function screen for a dialysis system of the present disclosure.

DETAILED DESCRIPTION

Dialysis patients desire machines or systems that tend to blend into the home environment rather than one that looks like a medical device. Many automated peritoneal dialysis ("APD") patients desire to have the APD instrument near their beds to facilitate interaction with the machine during the night, e.g., to read status, interpret and correct alerts, etc. It has been observed that in many patient use settings, the device is placed someplace other than the patient's nightstand. In some of those cases, the patient has reserved the nightstand for such items as an alarm clock, flower vase or light. The machine of the present disclosure provides room for these and others items and allows the APD instrument and the other items to be placed near the patient's sleep area. The instrument facilitates interaction with the machine, while allowing for the personal items to be present.

Patients commonly use APD devices in the bedroom while they and/or their partner sleeps. The instrument of the present disclosure also includes features that help the patient sleep more deeply and comfortably, promoting good health. The features can also directly help the patient's partner sleep better or indirectly help the partner by not waking the patient, who can wake the partner potentially.

Further, different patients have different tastes, styles and home settings. The APD machine of the present disclosure accordingly includes a machine capable of displaying one of multiple industrial designs and color schemes, instead of forcing a single design and scheme on the patient. The systems herein allow the patient to personalize their devices to fit better within the patient's particular home environment.

As discussed next, the instrument can also be programmed to wake the patient at a desired time and to ensure that a proper therapy has taken place prior to the wake time.

Figure 1:
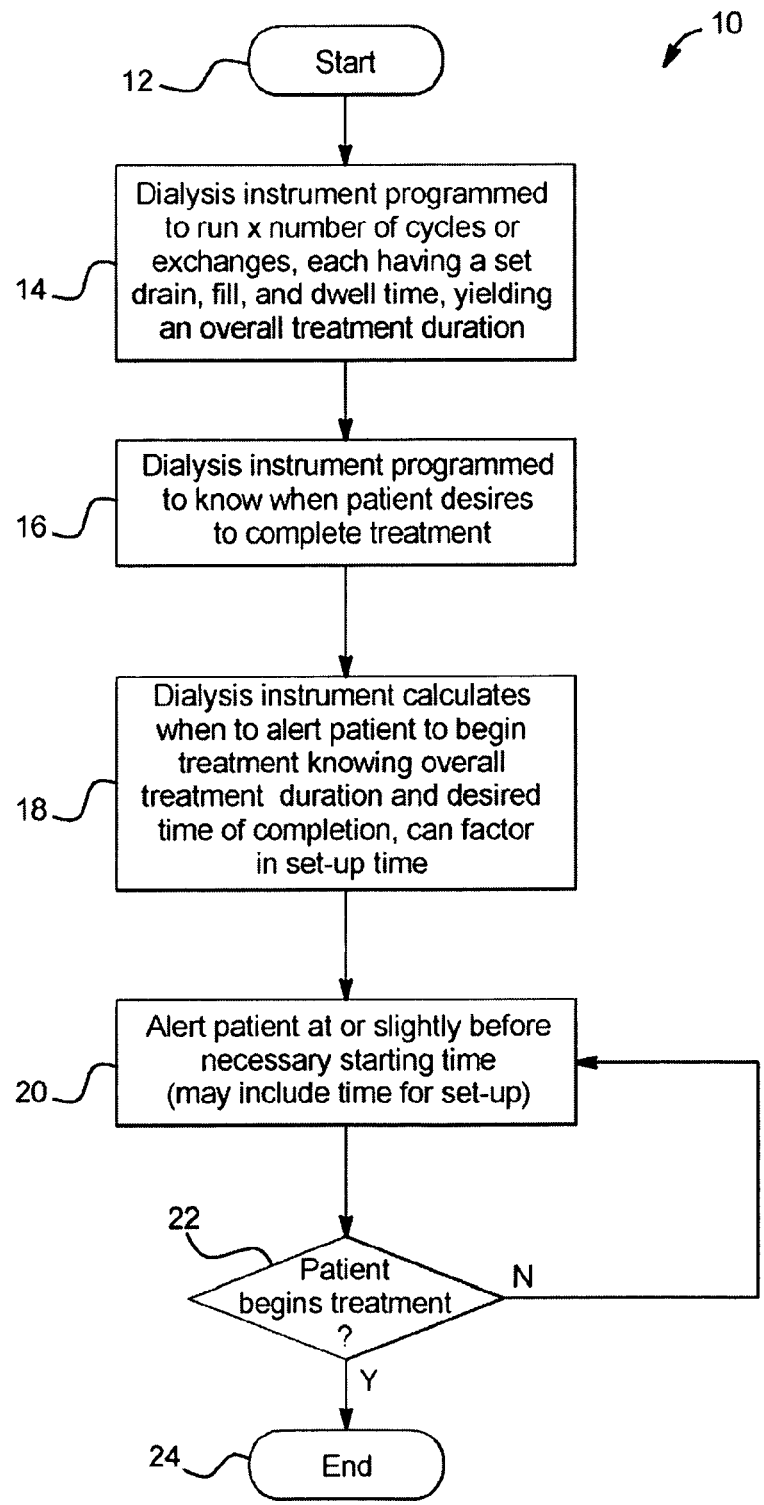
FIG. 1 is a schematic logic flow diagram illustrating one embodiment of a peritoneal dialysis system configured to alert the patient when it is time to begin treatment.

Referring now to the drawings and in particular to FIG. 1, logic flow sequence 10 illustrates one automated example for alerting or notifying the patient when it is time to begin treatment. Many peritoneal dialysis treatments are performed at home while the patient sleeps. While the fill, dwell and drain sequences discussed herein pertain to peritoneal dialysis ("PD"), the teachings of FIG. 1 apply also to a home hemodialysis treatment. Logic flow sequence 10 is run by a processor and memory located within the dialysis instrument or machine (see FIGS. 11 and 12). Sequence 10 as shown reminds the patient to begin therapy by a certain time, so that therapy is completed properly and the patient is able to end treatment at a desired time.

Upon starting sequence 10, as shown at oval 12, the dialysis instrument is programmed to run X number of cycles of exchanges. Each cycle or exchange has a set drain, fill and dwell time, which yields an overall treatment duration, as seen in connection with block 14. The drain, fill and dwell times are set in one embodiment by a clinician, nurse or doctor. Alternatively, the dialysis instrument provides the ability for the patients to manipulate the fill, dwell and drain times as shown herein. In either case, the drain, fill and dwell times are entered at step 14. Further alternatively, fill volume, drain volume and pump rate are entered and the fill time and drain time are outcomes for those parameters. In such case, fill and drain times are estimated via volume and rate.

As seen in connection with block 16, the dialysis instrument is also programmed to know when the patient desires to have treatment completed. Different embodiments for entering this information are shown below.

At block 18, the dialysis instrument calculates when to alert the patient to begin treatment knowing the overall treatment duration and the desired time of completion. In one embodiment, the processing and memory are configured to allow a predetermined amount of time for therapy setup, e.g., fifteen minutes. The predetermined amount of time can for example be set at the factory and later modified by the patient as the patient becomes more familiar with the therapy setup. The instrument alerts the patient to begin therapy setup fifteen minutes before therapy needs to begin to run the known fill, drain and dwell cycles a number of times to be completed by the patients desired completion time. At step 20, the dialysis instrument provides such an alert to the patient which can be an audio, visual or audiovisual alert, which signals the patient to begin therapy setup. The alert can be local or provide at or from the dialysis instrument. Alternatively, the alert is remote, e.g., sent via a wireless data link to the patient's cell phone or pager. The wireless data link can be via BlueTooth™ technology, for example.

Sequence 10 in connection with diamond 22 determines whether the patient has begun treatment. If the patient has not begun treatment, the dialysis system continues to provide the start therapy alert and a loop between block 20 and diamond 22 continues until the patient heeds the alert and begins treatment, at which time sequence 10 ends as seen in connection with oval 24.

Sequence 10 of FIG. 1 assumes preset dwell times, which each may be the same dwell time or the dwell times can differ. Sequence 50 of FIG. 2 allows the dwell times to be adjusted, so that the therapy is completed by the time that the patient sets. This can be done as long as a minimum dwell time for each cycle or exchange is provided. Sequence 50 starts at oval 52, wherein the dialysis instrument is programmed to run X number of cycles or exchanges. Each cycle or exchange having a set or calculated drain time and fill time, but wherein at least one of the dwell times if not more than one or all of the dwell times are adjustable, as seen in connection with block 54.

At block 56, the dialysis instrument is programmed to know when the patient desires to complete treatment. End time T2 is entered by the patient in various ways shown below, and as seen in connection with block 56. At block 58, the patient begins treatment at time T1, which is stored in the dialysis instrument. At diamond 60, sequence 50 determines whether a total treatment time equal to T2−T1 allows enough time for a minimum amount of dwell to occur given the set or estimated fill and drain times. Another way of stating this is that the dialysis instrument sets a lower dwell time limit and determines whether the total treatment time meets that limit based on the minimum dwell time plus the fill and drain times.

If the treatment time T2–T1 does not support or allow for enough dwell time, the dialysis instrument provides an audio, visual or audiovisual alarm to the patient as seen in connection with block 62, after which sequence 50 ends, as seen in connection with oval 68. If treatment time T2–T1 does support or allow for enough total dwell time, sequence 50 determines durations for each dwell type cycle based on treatment time (T2–T1), expected drain times and expected fill times to finish treatment by the patient ended time T2.

As discussed, the expected fill and drain times can be preset or be calculated based on known flowrate data and total volume filled and total volume drained. For example, assuming the fill flowrate to be constant, the total fill time is the total fill volume divided by the fill flowrate. Likewise, assuming a constant drain flowrate, a total drain time is the total drain volume divided by the average or constant drain flowrates. Fill and drain flowrates can vary, such that the flowrates can be averaged, wherein the average flowrate is used. It is also likely that the total drain volume will need to provide some estimation of the amount of excess water or ultrafiltrate that is removed from the patient. Thus, in one embodiment, the total drain volume is the fill volume of dialysate plus amounts of the patient's UF, which can be calculated knowing the patient's initial weight, the patient's dry weight and the average density of ultrafiltrate.

Figures 6A, 6B, 6C, 7:
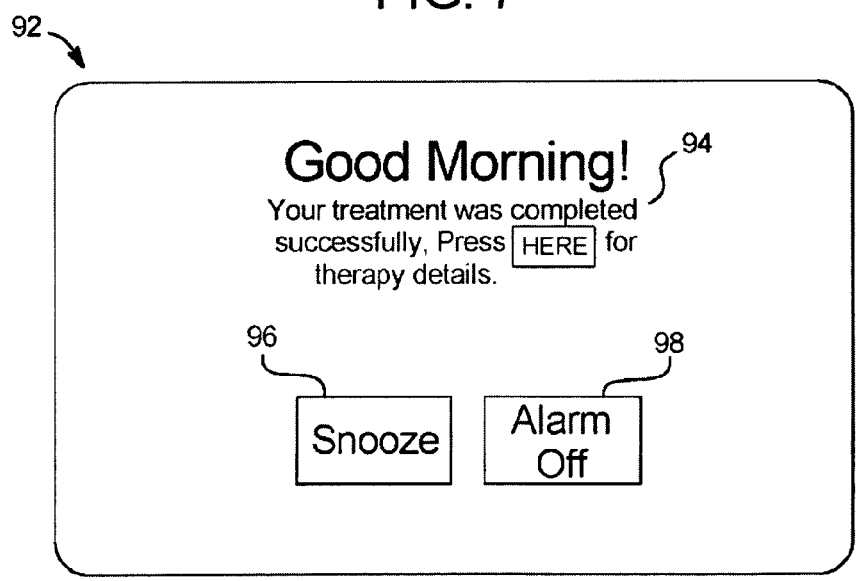
FIGS. 6A to 6C illustrate various dwell time distributions of the dialysis system of the present disclosure.
FIG. 7 is an elevation view illustrating yet another alarm feature screen for a dialysis system of the present disclosure.

FIGS. 6A to 6C below illustrate various dwell time distributions for dividing up the total dwell time calculated in connection with sequence 50. Once the individual dwell times are determined the treatment is performed as seen in connection with block 66 and sequence 60 ends as seen in connection with oval 68.

Figure 3:
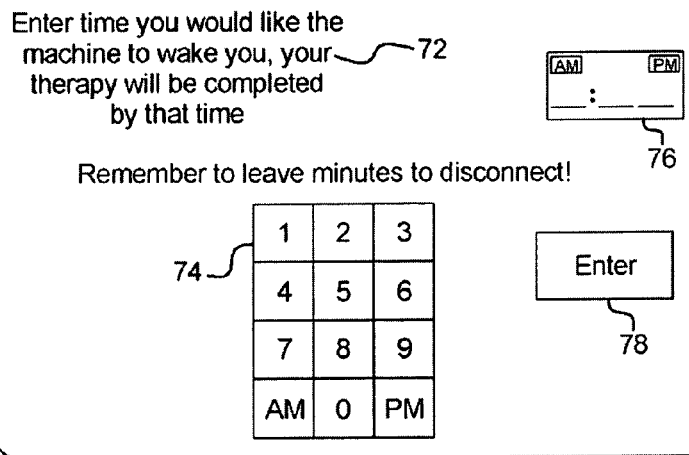
FIG. 3 is an elevation view illustrating an alarm feature screen for a dialysis system of the present disclosure.

Referring now to FIG. 3, a screen 70 from the dialysis instrument shows one embodiment for allowing the patient to enter the time that the patient wishes treatment to be completed, which is used in both sequences 10 and 50. Screen 70 can operate with a touch screen overlay and touch screen controller, which sends information entered onto screen 70 by the patient to processing in memory within the instrument to perform either of sequences 10 or 50. Alternatively, a portion or all of the items inputted into screen 70 are done offscreen via membrane switches or other type of electromechanical input devices.

Screen 70 displays a message 72, which can be audio, visual or audiovisual and which informs the patient to enter the time that the patient would like the machine to wake the patient and to remind the patient to leave enough time at the end of therapy to properly disconnect from the dialysis machine. Screen 70 displays a numeric keypad 74, which in an embodiment is a touch screen operated keypad. The patient enters the time in hours and minutes and sets whether such time is AM time or PM time. Screen 70 displays the entered time and whether the time is AM or PM at display area 76. If the patient is satisfied with the time and AM/PM setting, the patient presses enter 78 to advance to a next step in the therapy setup. In one embodiment, if the patient presses an incorrect or undesirable time before selecting enter 78, the patient can enter new numbers that are written over the old numbers. Alternatively, screen 70 provided a "back" input that allows the patient to erase a number and press a new number in its place.

Figure 4:
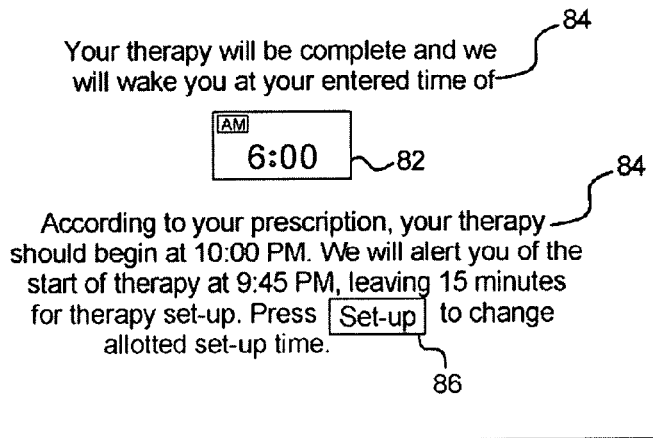
FIG. 4 is an elevation view illustrating another alarm feature screen for a dialysis system of the present disclosure.

Referring now to screen 80 of FIG. 4, the dialysis instrument after the patient enters the desired alarm time displays the alarm time in display area 82 and provides an audio, visual or audiovisual message 84 that the patient's therapy will be completed by the entered time and that the machine will wake the patient at that time. Message 84 further reminds the patient that according to the patient's prescription and the entered alarm time, the patient should begin therapy at or before 10:00 PM The machine accordingly alerts the patient at the start of therapy at 9:45 PM leaving a predetermined amount of time (e.g., 15 minutes) for therapy setup. Screen 80 provides an additional input device 86 that allows the patient to change the allotted setup time, e.g., for fifteen minutes to a different amount of time.

Figure 2:
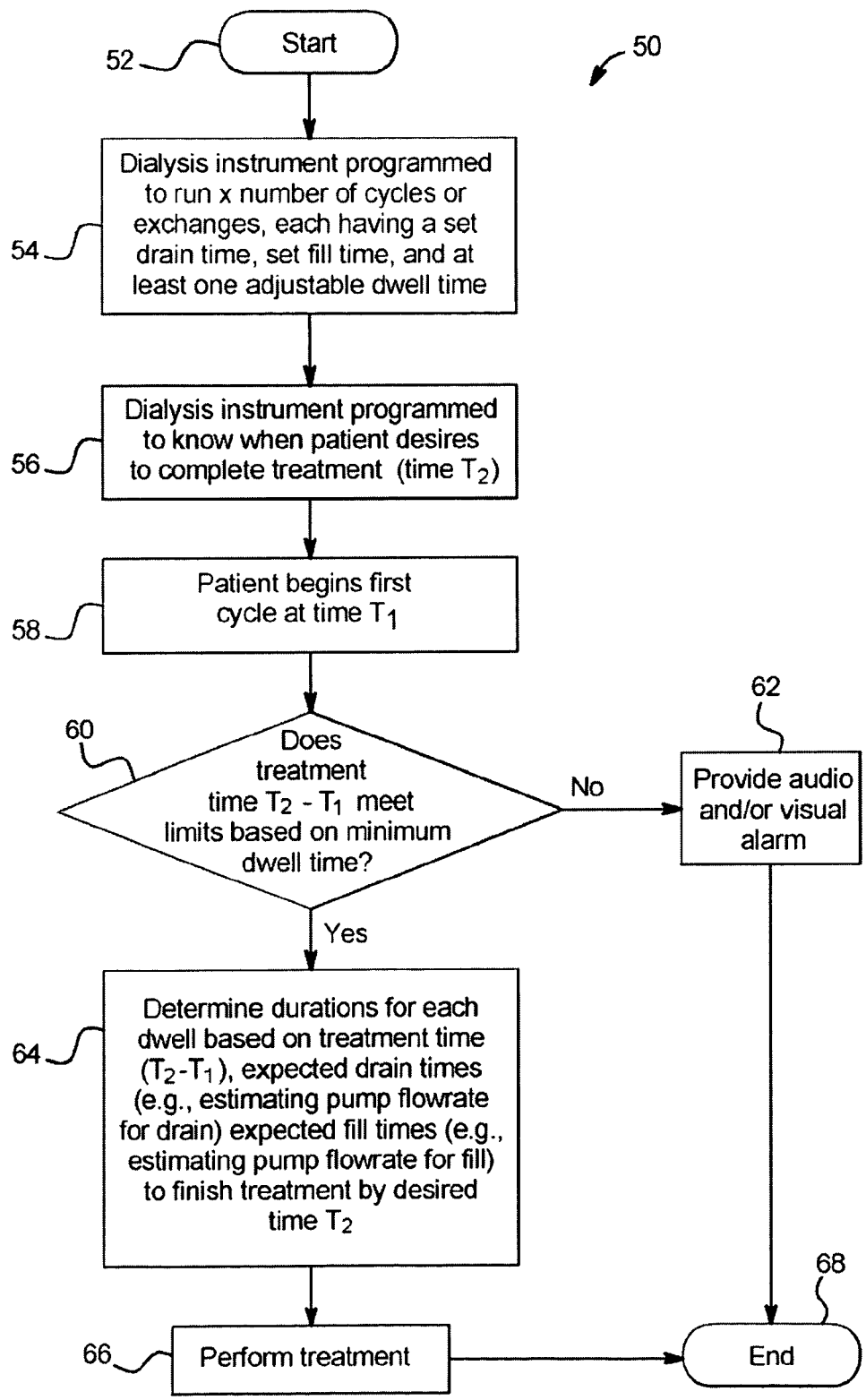
FIG. 2 is schematic logic flow diagram illustrating one embodiment of a peritoneal dialysis system configured to modify the dialysate dwell times to complete dialysis based on a starting time of the dialysis treatment.
Figure 5:
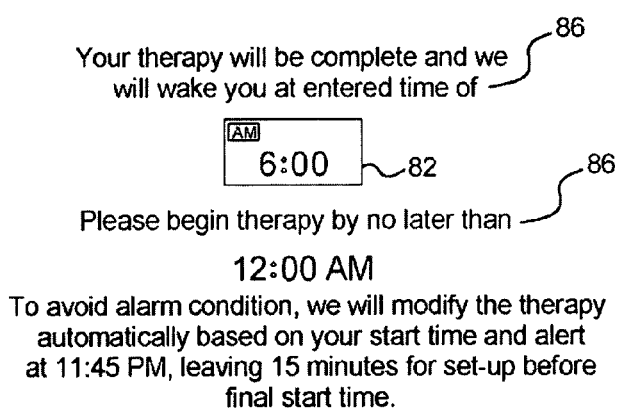
FIG. 5 is an elevation view illustrating a further alarm feature screen for a dialysis system of the present disclosure.

Screen 90 of FIG. 5 illustrates one implementation of sequence 50 of FIG. 2. Here again, the example alarm time or end of therapy time of 6:00 AM is illustrated in display area 82. An audio, visual or audiovisual message 86 informs the patient that the therapy will be complete at that time and also reminds the patient to begin therapy by no later than 12:00 AM to avoid an alarm condition, which is detected at diamond 60 of sequence 50, which occurs when the total amount of treatment time does not leave enough dwell time for an effective treatment. The machine also informs the patient that the machine will modify the therapy automatically based on the time that the patient actually starts therapy and alerts the patient at no later than 11:45 PM to begin treatment. Depending on the time that the patient actually starts therapy, the machine automatically adjusts the dwell times based on calculated or estimated fill and drain times.

Referring now to FIGS. 6A to 6C, various dwell distribution percentages are illustrated. The dwell distribution percentages are used for example in connection with sequence 50, in which a total dwell time is calculated using total treatment time, estimated or calculated total fill time and estimated or calculated total drain time. Once the total dwell time is known, the dwell time is split according to the distributions of FIGS. 6A to 6C. Each distribution assumes three exchanges or three dwell times, however, different numbers of exchanges can be used. Further, the distribution does not take into account the final fill, which is typically done in PD, wherein the final fill remains in the patient's peritoneum until the next treatment, which begins with a drain of the previous day's final fill. Thus, while three dwells are shown, the treatment would actually include four fills, the fourth fill being the last fill.

FIG. 6A shows a distribution in which the dwell times are equal. FIGS. 6B and 6C illustrate alternative distributions, which assume that the greatest amount of clearance occurs at the beginning of therapy when the amount of toxins and waste in the patients body are the highest. Front loading the dwell period allows the longest dwell time to occur when the patient is most toxic. Distribution of FIG. 6B splits the remaining dwell time between dwells two and three equally. The distribution of 6C shortens dwell three from dwell two, which in turn is shortened from dwell one.

Referring now to FIG. 7, screen 92 of the PD or HD system illustrates one embodiment of an alarm or wake-up screen of the present disclosure. An audible alarm from speakers 188 (FIGS. 11 and 12) can accompany screen 92. Screen 92 also displays an audio, visual or audiovisual message 94 that therapy has been completed successfully. Message 94 also incorporates an input (touchscreen or otherwise) that allows the patient to view therapy details. Screen 92 further includes additional alarm apparatus, namely, a snooze input 96 (touchscreen or otherwise) and an alarm of input 98 (touchscreen or otherwise). In one embodiment, the dialysis instrument continues to display message 94 during the snooze dwell period.

Referring now to FIG. 8, screen 100 of the PD or HD instrument illustrates a timer function. The timer function is provided to the patient as a reminder tool, for example, to allow patients to set a time to interrupt treatment for a desired purpose, such as to retrieve an item, pick-up a person, attend to a meal or other function or to perform any action needed, which is going to occur during the course of treatment (which can last up to eight hours for example). The timer function is likely used during the daytime while the patient is awake or resting, however, the timer function can be used during the night when the patient is sleeping to wake the patient for any desired purpose. Thus it is expressly contemplated to combine the timer function with the wake feature or use the timer function as the wake feature in the evening or at anytime at which the patient may need a prompting.

Screen 100 includes a message 102 indicating that the patient has selected the timer function. Keypad 74 (e.g., touch screen keypad) is provided. A start timer display 104 and a timer countdown display 106 are also provided. The timer function also includes enter input 78, which the patient presses to move to a different screen in the setup or operation of the dialysis machine.

The patient enters a time for the timing function or countdown to begin using keypad 74 to punch the time in hours and minutes. The entered time is displayed in timer start time display 104. The entry of the timer start time is performed and displayed in the same manner as the alarm awake time entered via keyboard 74 and displayed via display area 76 as discussed above in connection with screen 70. The patient then enters in a similar manner the amount of countdown time in hours and minutes, which is displayed in timer countdown time display 106. Although not illustrated, individual visual, audio, audiovisual messages can be provided to prompt the patient to enter in sequence the timer start time and the timer countdown time. Alternatively, either setting can be made prior to the other.

Once the patient enters the timer start time and the timer countdown time and confirms entry via enter button 78, the dialysis machine begins the timer countdown at the designated time and counts down an amount of time entered at display 106. At the end of the countdown, the machine can be configured to provide an audio, visual or audiovisual alert to the patient. The machine at the end of the countdown can also display a cancel or end alarm input that allows the patient to stop the alarm or alert and continue with any desired activity.

Referring now to FIG. 9, screen 110 illustrates one embodiment of a calendar function, which can be implemented in the dialysis instrument of the present disclosure. Screen 110 includes a message 112, which audibly, visually or audiovisually informs the patient that the patient has selected the calendar function. In the illustrated embodiment, the calendar function operates with a touch screen overlay as discussed above. Alternatively soft keys or dedicated membrane switches are used to enter information into the calendar function.

Message 112 informs the patient to touch a date to make the date enlarge, so that information can be entered or edited in the enlarged date. A keyboard provided by the instrument (touch screen keyboard or keyboard via embodiments shown in connection with FIGS. 11 and 12) is used to enter the information. When the patient is finished entering or editing information within the enlarged date, the patient touches the enlarged date which then shrinks back to its original size and position. Message 112 also indicates to the user that the processing and memory within the dialysis instrument retains the information entered into the calendar, so that the information will be displayed the next time the patient recalls the calendar function and even after one or more power down.

The calendar function on screen 110 also includes month inputs 114, which allow the user to select a particular month to view and edit. In the illustrated embodiment, the selected month, May, is highlighted along the row of inputs 114. The selected month and year are also shown on the sides of calendar 116. Inputs 114 include arrow keys that are provided for shifting the months into past or future years. Calendar 116 includes each of the days of the week and each of the days of the particular month for the particular year.

The selected month of May illustrates example entries that the patient has made. For example, the patient has entered for a reminder that there is a doctor's appointment on the Ninth of May. The patient is scheduled to baby-sit on May 19. A birthday is to occur on May 22, and the patient is on vacation from May 29 to May 31.

It is also contemplated that when the date is selected and enlarged, a twelve hour or twenty-four hour time entry menu is displayed, such that the patient can enter a particular time for the doctor's appointment, babysitting, birthday party, flight times, etc., for a given day. The patient uses a keyboard entry via one of the embodiments discussed below to enter the specific time information. It is accordingly further contemplated that the dialysis machine provide an alarm or alert to the patient at a prescribed time before the particular time entry. For example, if the patient's doctor's appointment is 11:00 AM, it is contemplated to program dialysis machine to alert the patient at 10:30 AM or 10:45 AM to remind the patient of the appointment.

Figure 10:
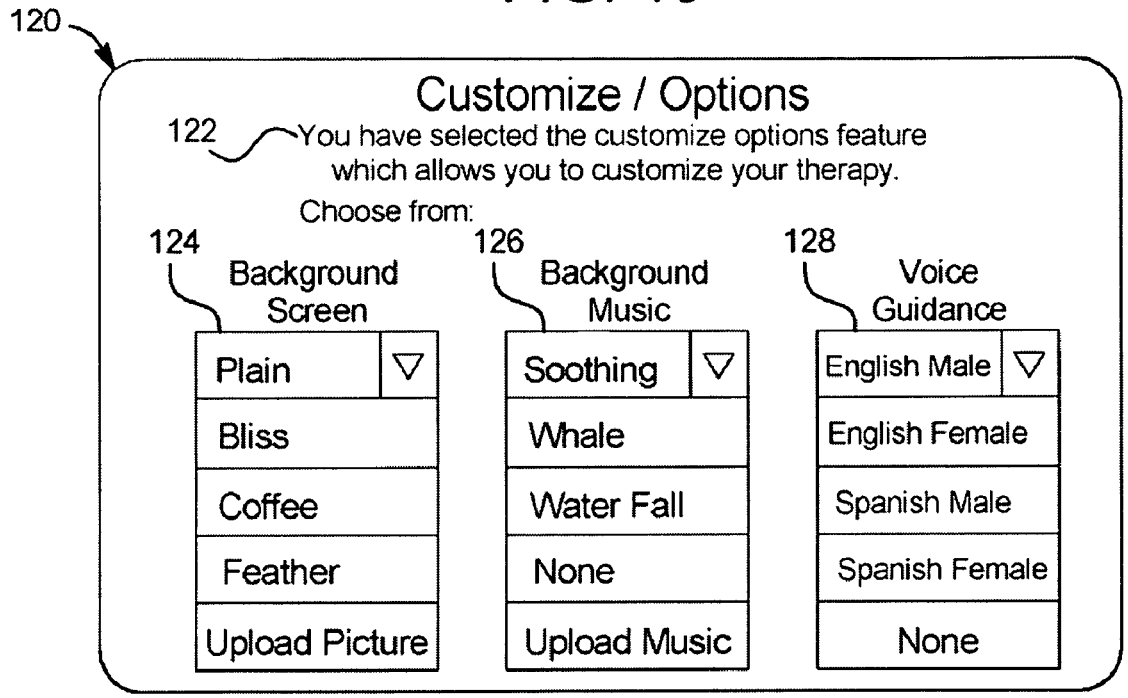
FIG. 10 is an elevation view illustrating a customize options screen for a dialysis system of the present disclosure.

Referring now to FIG. 10, screen 120 of the dialysis instrument illustrates one embodiment for a customize/options feature of the dialysis system of the present disclosure. Screen 120 is again implemented in one embodiment using a touch screen overlay but is alternatively maneuvered through via soft keys or membrane switches. Screen 120 includes an audio, visual or audiovisual message 122 that informs a patient that the patient has selected the customize options feature, which allows the patient to customize the machine and therapy. In the illustrated embodiment, the customize/options feature allows the patient to customize any one or more of a background screen at drop menu 124, background music via a background music menu 126 and a voice for a voice guidance feature via voice guidance dropdown menu 128.

In one embodiment, the processing and memory are configured such that when the patient presses the arrow associated with any of menus 124, 126 and 128, the associated selections or options appear. Before such time, menus 124, 126 and 128 show only the currently selected background screen, background music and voice for the voice guidance feature. Each menu 124, 126 and 128 is shown having five options. More or less options can be provided. Further, the displayed options are for illustration purposes only and can also be modified as desired.

In the illustrated background dropdown menu 124, the patient can choose between a plain background, a bliss background, a coffee background, a feather background or a upload picture option, which allows the patient to upload a picture onto the instrument screen as the background. When the patient selects the upload picture feature, the customize option screen prompts the user to make a data communications connection, such as a serial connection to a computer or camera, a modem connection to an internet or a wireless connection to a data output source, to transfer a desired background to screen 120.

Likewise, the background music dropdown menu 126 shows various selections, such as soothing background music, whale calls, waterfall, a no background music option and a customize background music option. Selecting the customize or upload music option causes screen 120 to prompt the user again to connect via any of the above data communication modes to a device capable of storing music, such as a computer, MP3™ player, ipod™ music player, etc.

The voice guidance dropdown menu 128 of customize/options screen 120 allows the patient to select a voice that audibly guides the user through therapy setup, procedures taken at the end of therapy, and possibly for alerts occurring during therapy (also sets language for text messages appearing on the screens described herein). Example voice guidance selections on dropdown menu 128 include an English speaking male, an English speaking female, a Spanish speaking male, and a Spanish speaking female. Other languages can be added or used instead as desired. Further, the patient can select via customize/options the option of having no voice guidance at menu 128, which would set English as the default setting for the text messages or invoke a sub-menu that allows the user to select a language for text messages.

Figure 11:
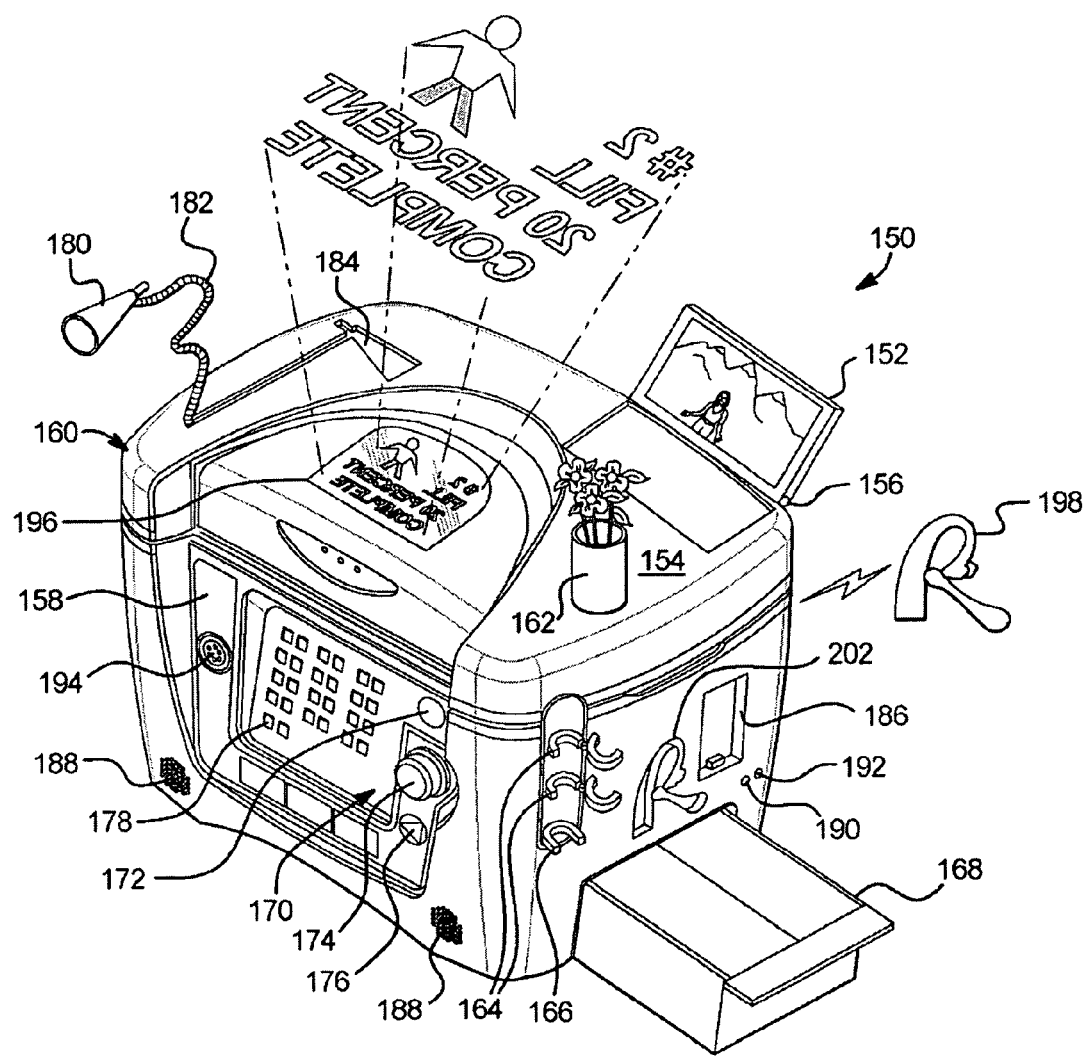
FIG. 11 is a perspective view of one embodiment of a dialysis instrument having multiple patient-assist features.
Figure 12:
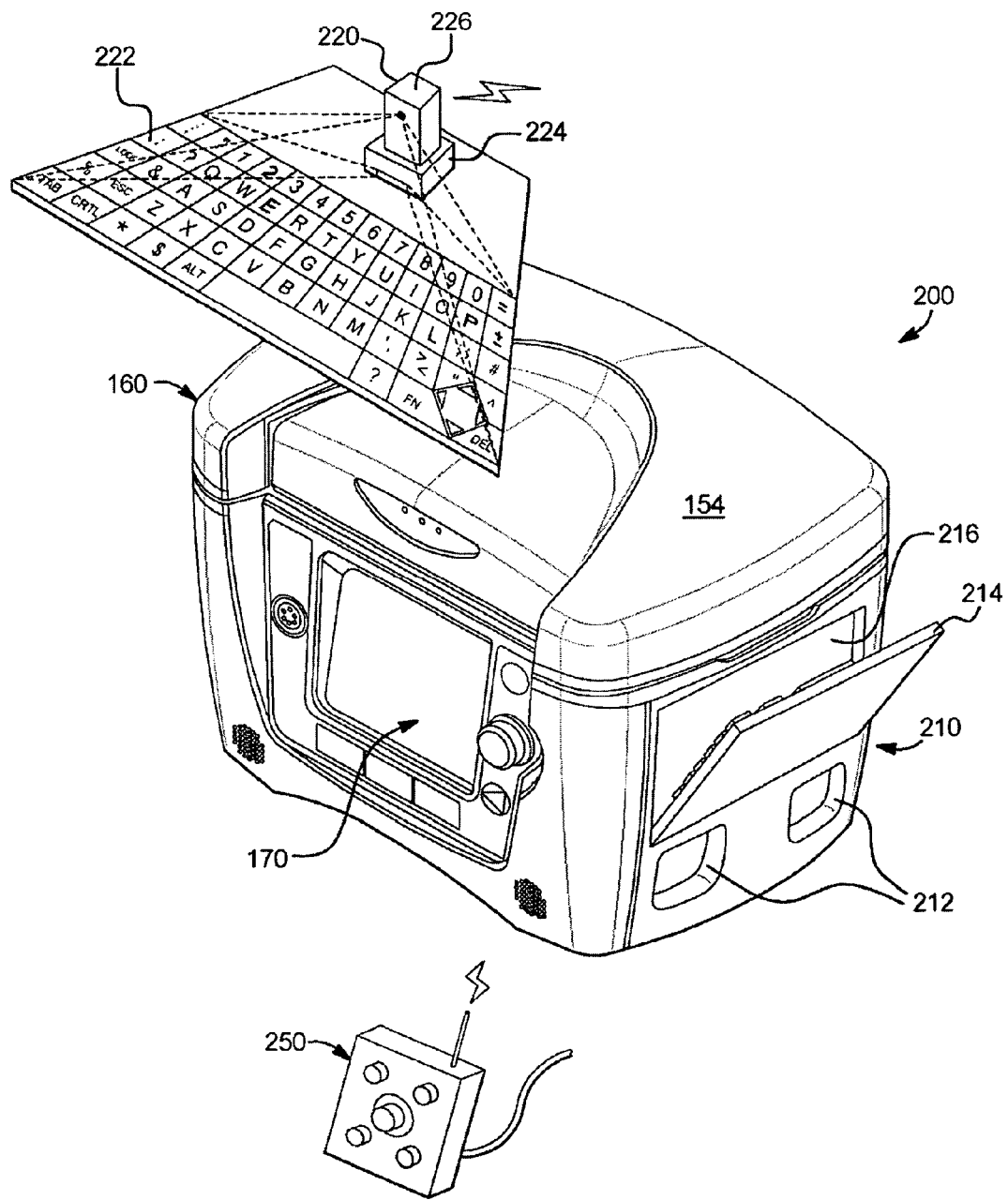
FIG. 12 is a perspective view of another embodiment of a dialysis instrument having multiple patient-assist features.

Referring now to FIG. 11, dialysis instrument 150 illustrates many additional patient friendly features for the dialysis system of the present disclosure. Dialysis system 150 does not have to include each of the features shown herein, however, FIG. 11 illustrates one embodiment for each of the features. Further, it is contemplated to combine at least some of the features of dialysis system 150 of FIG. 11 with those of the system 200 of FIG. 12. The goal or intent of the features shown in connection with FIGS. 11 and 12 is to make the dialysis instrument more personalized, easier to use, more enjoyable to use and/or more effective.

To allow the patient to personalize the dialysis instrument, dialysis instrument 150 in one implementation is provided with a photograph holder 152. Photograph holder 152 is shown being connected hingedly to a top surface 154 of dialysis instrument 150 via a hinged connection 156. Thus, picture holder 152 can be folded down and out of the way if not used. FIG. 11 shows picture holder 152 in use, which allows the patient to insert one or more photographs to personalize the instrument and treatment. While dialysis instrument 150 is shown as having a single picture frame 152, it is contemplated to provide multiple picture frames with instrument 150.

Housing 160 of instrument 150 is further modified to include a flower or writing utensil holder 162. Utensil holder 162 can be formed integrally with top 154 of housing 160 or be formed separately from housing 160 and configured to be removably attached to top 154.

Dialysis instrument 150 also includes a customizable or selectable front bezel 158, which the patient can choose to match the patient's environment or to otherwise personalized instrument 150. Bezel 158 can be selected at the time instrument 150 is ordered and fitted at the manufacturing facility. Alternatively, bezel 158 can be removed and replaced readily by the patient and switched at different times as the patient desires. Likewise, it is contemplated to provide the outer shell or housing 160 of dialysis instrument 150 in a color or colors that the patient desires. Besides color, the decorative bezel 158 can also simulate various material patterns and finishes (e.g., wood, stone, floral pattern, etc.) to match the domestic environment.

Instrument 150 includes a display device 170, which as described above operates in one embodiment with a touch screen overlay. Display device 170 as illustrated above selectively displays other personalizing features or options, such as patient selectable screensavers, wallpaper, backgrounds, etc. It is contemplated to provide the touch screen overlay with tactile feedback to produce a touch screen button 172, which when pressed provides tactile feedback to the patient or user. One apparatus for providing a touch screen with tactile feedback is discussed in U.S. Pat. No. 5,412,189, entitled, "Touch Screen Apparatus With Tactile Information", the entire contents of which are incorporated herein by reference.

In the patent, tactile information (31 to 34) is molded into a touch screen surface (30) when the touch screen surface is initially manufactured. An example is given in which if the touch screen surface (30) is made of glass, molten glass is forced into a mold that includes tactile information (31 to 34). Another method of connecting the tactile information (31 to 34) to touch screen surface 30 discussed in the patent is to cover the touch screen surface (30) with a clear plastic sheet having tactile information (31 to 34) molded or punched thereon. For example, the plastic sheet could be pressed in a mold containing the tactile information, heated to deform the plastic sheet to the shape of the mold, and allowed to cool. This plastic sheet can then cover all or some of the touch screen surface, affixed either by surface tension or adhesive.

It is understood by the inventors of the present disclosure that touch screens are typically plastic overlays that are connected to the glass of the video monitor. Thus the present inventors contemplate an additional embodiment in which the "tactile information" or tactile bumps are molded into the touch screen overlay itself. The touch screen overlay with integral tactile bumps is then attached to the video monitor in the standard manner. Here, an additional plastic sheet is not needed.

A further alternative method disclosed in the patent is to apply small drops of clear epoxy to the touch screen surface (30) to form the tactile information (31 to 34). Here, a mask is used to insure proper positioning of the tactile information on touch screen surface (30). The epoxy is disclosed as being selected so as to dry to a relatively transparent consistency so as not to unacceptably interfere with the appearance of any visual data underneath the tactile information. Lens effect errors are disclosed as being minimal as long as the tactile information is not overly large.

The tactile information or bumps 178 are set at various X-Y positions on the display device 170 of FIG. 11. Tactile information or bumps 178 can be shown in connection with any information useful for instrument 150. For example one of the tactile bumps 178 can be associated with a first displayed selection on a first screen. The same tactile bump 178 is then associated with a second displayed selection on a second screen of display device 170. Even when tactile information or bumps 178 are Braille keys or characters as discussed below, the Braille keys can form the words "yes" and "no" and accordingly be associated at different times with different therapy queries, such as therapy setup questions, that each can be answered with either a "yes" or a "no".

As discussed, instrument 150 includes or can include off screen input devices, such as a dial 174 or membrane switch 176. In one embodiment, membrane switch 176 operates as a soft key to provide different input functionality based on different information displayed on display device 170. Accordingly, membrane switch 176 includes an arrow that points to a particular region of the display screen that may contain varying text or graphics depending on the function/feature currently associated with the membrane switch.

FIG. 11 illustrates one option for modifying instrument 150 to be more easily used by blind patients. Here, Braille keys or characters 178, which can be affixed to or formed with the touchscreen overlay, are raised or offset from the overlay surface a distance sufficient such that the mere touching of a Braille key 178 is not sufficient to enter an input into machine 150 to protect against inadvertent swipes. However, a pressing or pressure applied to a particular key 178 is sufficient to cause a change in capacitance or resistance at the corresponding X-Y coordinate of the particular Braille key, which is sensed and which causes the input of that character to be placed into memory and used by a processor for inputting data into instrument 150. In this manner, blind patients or patients that are visually impaired can communicate information to instrument 150 to setup therapy, modify therapy, or even to send a message from instrument 150 through an electronic mail or over the internet to an on-call clinician or physician.

Besides the "yes" and "no" Braille keys, it is contemplated to provide a Braille keypad for the patient to enter information. Here, the display of Arabic numbers beneath or directly adjacent to the corresponding Braille character would likely be fixed from screen to screen.

Instrument 150 also includes clamps or clamping devices 164 that are sized to hold and clamp a patient line, which extends for example from a disposable cassette loaded into instrument 150. As discussed above, the patient if awake can halt or interrupt a treatment if needed. To do so, a patient performing PD disconnects the patient line from a catheter that is implanted into the patient's peritoneum. Clamps 164 allow the patient to place the patient tube against housing 160 of instrument 150 and clamp the patient line, so that fresh dialysis fluid is not wasted and to prevent fluid from leaking from the disposable unit placed inside instrument 150. Clamps 164 also act to preserve the sterility or cleanliness of the disposable unit.

In certain instances, the patient has to break or sever a frangible seal that is placed inside a piece of tubing, for example inside the patient line. Certain patients, especially elderly patients, can have difficulty breaking the frangible. In one embodiment therefore instrument 150 includes a member 166 which can fold down from housing 160, and which the patient uses to provide leverage against which to break the frangible. In the illustrated embodiment, member 166 includes a pair of legs. The tube at the frangible section is wedged below one of the legs and above the other of the legs to provide leverage against which to bend the tube and break the frangible seal. Member 166 is used alternatively and/or configured alternatively to assist in either gripping twist caps or pulling pull caps from an associated container.

In the illustrated embodiment, dialysis instrument 150 also includes a drawer 168, which the patient can open to insert or retrieve therapy supplies, an automated or manual patient-line connection device or other items that the patient wishes to store at or near dialysis instrument 150. In the illustrated embodiment, drawer 168 slides into instrument 150 when not in use, such that the drawer is kept out of the way when not needed. A tab or other locking device can be provided to lock drawer 168 in place when instrument 150 is being moved, for example.

Instrument 150 of FIG. 11 is also fitted with a light or lamp 180, which can be a reading light, light emitting diode ("LED"), night light and have any suitable intensity and size. In the illustrated embodiment, light 180 is attached to top 154 of housing 160 via an armor coated wire which can be bent and formed so that light 180 can be fixed at a desired position. Further, light 180 can be tilted towards and away from the patient to adjust the amount of light directed at the patient. In the illustrated embodiment, top 154 includes a groove or aperture 184 for accepting positionable cord 182 and light 180, so that the light and cord tuck out of the way and do not appreciably increase the overall size and profile of instrument 150. While light 180 is shown connected via armor plated cord 182 to top 154 of dialysis instrument 150, it is contemplated to attach light to other surfaces of housing 160, such as one of the sides or back of the housing.

It should be appreciated that groove or aperture 184, writing utensil holder 162, and picture frame 152 are shown at the top of instrument 150 for ease of illustration. Placing crevices, grooves and other liquid collecting structures as the top of the instrument could lead to the wetting of components within the instrument. Accordingly, one or more of these features is fixed alternatively to one of the sides of instrument 150. Also, groove or aperture 184, for example, can be replaced with a clip into which cord 182 of lamp 180 snap-fits.

Instrument 150 also includes a number of electronic features, which make the dialysis instrument and treatment easier to learn and use and more effective. In one embodiment, instrument 150 is provided with a charging and docking station 186 that allows the patient to dock and charge the patient's MP3™ player, ipod™ player or other music storage device to charge the device and/or play music from the device, for example through speakers 188 located inside instrument 150. Instrument 150 also includes an audio line output 190 that allows the music to be sent from the instrument to external speakers. Instrument 150 further includes an audio line input 192 that accepts sound or music from an external source and plays the sound or music through speakers 188. Speakers 188 are also configured to output the voice guidance and internally stored background music discussed above in connection with FIG. 10. It is further contemplated to provide a music storage device within dialysis instrument 150, wherein a data connection between instrument 150 and a song providing outlet, such as the internet, enable instrument 150 to download songs for direct storage into memory of instrument 150.

As discussed above, instrument 150 in one embodiment provides voice guidance to the patient or user. It is also contemplated that instrument 150 receive voice instruction from the patient or user. For example, in addition to or instead of Braille keys 178, the voice recognition software can greatly enhance the interaction of device 150 with blind or visually impaired patients. Further, voice data input can be a preferred option for any patient who desires to input data, while having hands free to perform other duties. Accordingly, instrument 150 in one embodiment includes a microphone 194 that accepts audible commands from the patient or user. The output of microphone 194 is coupled to a processor within instrument 150, which processes the audible input using software to convert the audible command to a data input into machine 150. It is further contemplated to provide voice recognition software that prevents outside noise or people other than the patient or clinician from making changes to therapy settings within instrument 150.

Instrument 50 illustrates a further electronic feature for enhancing the operability and effectiveness of the dialysis instrument and treatment. Here, instrument 150 is provided with a light projecting apparatus 196 that projects information from the machine onto a surface that the patient can view more readily than screen 170. For example, projector 196 can project information onto a wall or ceiling of the room in which instrument 150 is positioned. The information projected via projector 196 can include the time of day, date, ambient temperature or any information related to an ongoing treatment. For example, FIG. 11 shows treatment data both numerically and graphically. Here, projector 196 projects information relating to the current status of a treatment which is undergoing a second fill that is twenty percent complete. This information is conveyed both via text and numbers and via a graphic of a human body, which is approximately twenty percent colored. Thus a patient lying in bed can quickly glance at, e.g., the ceiling, if the patient wakes up or looks up from a television to quickly discern what point in the treatment is occurring.

It is contemplated for projector 196 to operate with processing and memory within instrument 150 to scroll through a series of different displays, for example, displaying time and date at one moment, displaying ambient temperature at another moment, displaying therapy information, such as that shown in FIG. 11, at a third moment, and repeating this cycle, so that the patient can view different data without having to physically push a button to change the information displayed. Still further, it is contemplated to provide the patient with a tethered or wireless remote device that allows the patient to scroll through or to pick a desired set of information. The information can be displayed in a single color, such as red or in multiple colors, such as red, green and blue.

Technology for projector 196 currently exists as described for example in U.S. Pat. No. 7,252,394, entitled Laser Projection Display And Illumination Device With MEMS Scanning Mirror For Indoor And Outdoor Applications, assigned on its face to Advanced NuMicro Systems, Inc. (San Jose, Calif.), the entire contents of which are incorporated herein by reference. In this patent, a projection display system includes a light source emitting a light beam, and a reflecting mirror system for scanning the light beam over an image to illuminate the image. The light source can be solid state such as a laser diode operable with a one or more microelectromechanical systems ("MEMS") scanning mirrors that rotate to raster scan the light beam over the image.

Instrument 150 of FIG. 11 further includes wireless capability which can send and receive information to and from the patient via any suitable wireless communication technology, such as WiFi™, Bluetooth™, Zigbee™ or infrared technology. System 150 can be outfitted with a wireless headset 198 that includes both a speaker for transmitting sound to the patient and a microphone for accepting sound from the patient. Machine 150 in the illustrated embodiment further includes a groove or channel 202 sized and shaped to accept headset 198 when not in use.

Referring now to FIG. 12, instrument 200 illustrates additional features configured to enhance the usability and effectiveness of the dialysis instrument and a treatment. Again, various features shown in connection with instrument 200 can be combined with various features shown in connection with instrument 150 of FIG. 11 and vice versa. Instrument 150 illustrates certain features configured to aid a blind or visually impaired patient. Instrument 200 of FIG. 12 includes a telecommunications device for the deaf ("TDD") 210, which is an electronic device for text communication via a telephone line, used when one or more of the parties has hearing or speech difficulties. TDD 210 is known and is sometimes referred to as a telephone typewriter or teletypewriter ("TTY"), text-phone (common in Europe and the United Kingdom) and mini-com (United Kingdom). TDD 210 includes a phone holder 212, which accepts and holds microphone and speaker portions of a telephone. TDD 210 of instrument 200 further includes a fold down keyboard, which the hearing or speech impaired patient uses to type text into instrument 200.

Instrument 200 includes processing and memory that convert the text into a voice output, which is inputted into the microphone of the telephone inserted into telephone holder 212. Fold down keyboard 214 in one embodiment exposes a display device 216, which displays text that is converted from a voice communicating over the telephone through the speaker of the phone and into a microphone imbedded in one of the phone holding cavities 212. The processing and memory are further configured to convert this information to text displayed on secondary display device 216. Secondary display device 216 can be provided in place of display device 170 or in addition to that display device. TDD 210 can be provided on any suitable surface of instrument 200.

Instrument 200 further includes a projection device 220, which in the illustrated embodiment is located on a surface onto which a virtual keyboard 222 is projected. Projection device 220 communicates wirelessly with instrument 200 in one embodiment. Virtual keyboard 220 as illustrated includes all the letters, numbers and many of the symbols including punctuation, navigational symbols, and other symbols, of a standard keyboard.

One suitable keyboard projector of projector 220 is an I-Tech VKB laser keyboard manufactured by Hutchison Harbour Ring Limited—HHR, a subsidiary of Hutchison Whampoa Limited ("HWL"). This laser keyboard projector is about the size of a cellular phone (e.g., 90 mm×34 mm×24 mm), which is connected to instrument 200 via a positionable cord 182. Projector 220 in the illustrated embodiment snaps onto a board 224 via a snap holder 226 located on the board. The projection surface does not have to be board 224 and can for example be any board, tabletop or book that is relatively smooth, e.g., does not have projections from the surface greater than one millimeter. Snap holder 226 however allows board 224 to be tilted so that the patient can place board 224 on a pillow, which is in turn laid over the patient's stomach when lying in bed. Or, board 224 can be laid in the patient's lap when sitting.

Projector 200 and virtual keyboard 222 enable users to type text into instrument 200, e.g., to enter therapy information into the instrument or to send electronic mail. Projector 200 sends data wirelessly to instrument 200 in one embodiment, e.g., via WiFi™, Bluetooth or Zigbee™ technology. Instrument 200 in turn is configured to be connected to a modem, which allows the instrument to access an internet and to send electronic mail.

The above-referenced laser projector uses direction technology based on an optical recognition mechanism, which enables the user to tap on the projected keys. The projector makes a tapping or clicking noise when a virtual key is touched, providing audible feedback and simulating a real keyboard. The tapping or clicking noise can be deactivated for bedtime use if desired. The laser projector projects a template of the keyboard interface onto an adjacent interface surface. The template is produced by illuminating a holographic optical element with a red diode laser. The keyboard template serves only as a reference for the user and is not involved in the detection process. That is, in a fixed environment, the template could alternatively be printed onto the interface surface or board.

The projector also projects an infrared plane of light that is generated just above, and parallel to, the interface surface. The plane of light is invisible to the user and hovers a few millimeters above the surface. When the user touches a key position on the interface surface light is reflected from the plane in the vicinity of the key and is directed towards the sensor module. Reflected light from user interactions with the interface surface is passed through an infrared filter and imaged on to a complimenatary metal-oxide semiconductor ("CMOS") image sensor in the sensor module. Hardware embedded in the sensor chip makes a real-time determination of the location of the reflected light. The location is correlated to a keyboard character or function, which is entered into a memory or buffer of dialysis instrument as data. The processing of projector can track multiple reflection events simultaneously and can thus support both multiple keystrokes and overlapping cursor control inputs.

Symbols selected via virtual keyboard 222 can be displayed for example on main display screen 170 or projected on the ceiling, wall, furniture etc. Also, instrument 200 can be configured to read the typed characters aloud. The patient can be away from instrument 200 and still input information into the instrument. For example, the patient can be lying in bed and facing away from the dialysis instrument 200 and still enter information into the instrument and have text displayed on the instrument. The patient can thereby enter information into dialysis instrument 200 without turning towards the instrument and disrupting comfortable sleep or relaxing position. In one embodiment, however, dialysis instrument is configured such that the patient has to review and confirm all data entered via projector/virtual keyboard, e.g., at display device 170 of instrument 200, before the machine operates according to the data.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis machine comprising:
an enclosure;
dialysate pump located within the enclosure;
a graphical user interface ("GUI") integrated into the enclosure and configured to display a parameter associated with the dialysate pump; and
a projector integrated into the enclosure and configured to project a parameter onto a surface external from the enclosure so as to allow a patient to readily view the parameter,
wherein the GUI is configured to display the displayed parameter and the projector is configured to project the projected parameter simultaneously.

2. The dialysis machine of claim 1, wherein the parameter is selected from the group consisting of (i) total pump fill; (ii) total pump dwell time; (iii) total pump drain;
(iv) pump fill remaining; (v) pump dwell remaining; (vi) pump drain remaining; (vii) total number of fill/dwell/drain cycles; and (viii) current fill/dwell/drain cycle.

3. The dialysis machine of claim 1, the graphical user interface and projector further operable to display at least one of: (i) the current time, (ii) ambient temperature, (iii) total ultrafiltration removed, and (iv) a time remaining for treatment.

4. The dialysis machine of claim 1, which includes a switch configured so that the patient can selectively project the parameter onto the surface.

5. The dialysis machine of claim 1, which includes a remote device configured to operate with the GUI, so as to navigate to and modify the displayed and projected parameter.

6. The dialysis machine of claim 5, the GUI and projector further configured to display and project, respectively, the modified parameter.

7. The dialysis machine of claim 5, the remote device communicating with the GUI via wired or wireless communication.

8. The dialysis machine of claim 1, wherein the displayed parameter and the projected parameter are different parameters.

9. The dialysis machine of claim 1, wherein the displayed parameter and the projected parameter are the same parameter.

10. The dialysis machine of claim 1, wherein the projector is integrated into a top surface of the enclosure.

11. The dialysis machine of claim 10, wherein the projected parameter is projected upwardly.

12. The dialysis machine of claim 1, wherein the GUI is situated on a side surface of the enclosure and the projector is situated on a top surface of the enclosure.

13. The dialysis machine of claim 1, which includes a remote device configured to operate with the GUI, so as to navigate to and modify at least one of the displayed and projected parameters.

14. The dialysis machine of claim 13, the GUI and projector further configured to display and project, respectively, the modified parameter.

15. The dialysis machine of claim 13, wherein the remote device communicates with the GUI via wired or wireless communication.

16. A dialysis machine comprising:
an enclosure;
dialysate pump located within the enclosure;
a graphical user interface ("GUI") connected to the enclosure and configured to display a parameter associated with the dialysate pump;
a projector integrated into the enclosure and configured to project a parameter onto a surface external from the enclosure so as to allow a patient to readily view the parameter; and
a virtual keyboard projector separate from the enclosure, the virtual keyboard projector configured to project a virtual keyboard on another surface external from the enclosure, wherein:
the patient is enabled to interact with the projected virtual keyboard to input data, and
the virtual keyboard projector is configured to wirelessly communicate the inputted data to the dialysis machine and the GUI.

17. The dialysis machine of claim 16, wherein the parameter is selected from the group consisting of: (i) total pump fill; (ii) total pump dwell time; (iii) total pump drain; (iv) pump fill remaining; (v) pump dwell remaining; (vi) pump drain remaining;
(vii) total number of fill/dwell/drain cycles; and (viii) current fill/dwell/drain cycle.

18. The dialysis machine of claim 16, wherein the graphical user interface and the projector are further configured to display at least one of: (i) the current time, (ii) ambient temperature, (iii) total ultrafiltration removed, and (iv) a time remaining for treatment.

19. The dialysis machine of claim 16, which includes a switch in operable communication with the projector so that the patient can selectively project the parameter onto the surface.

* * * * *